United States Patent [19]

Hoffa et al.

[11] 4,086,061

[45] Apr. 25, 1978

[54] TEMPERATURE CONTROL SYSTEM FOR CHEMICAL REACTION CELL

[75] Inventors: Jack L. Hoffa, Brea; Robert A. Ray, Fullerton, both of Calif.

[73] Assignee: Beckman Instruments, Inc., Fullerton, Calif.

[21] Appl. No.: 772,410

[22] Filed: Feb. 28, 1977

[51] Int. Cl.² .................. G01N 33/16; G01N 1/14
[52] U.S. Cl. .......................... 23/259; 23/253 R; 165/18
[58] Field of Search ............ 23/292, 259, 252, 253 R; 165/18

[56] References Cited

U.S. PATENT DOCUMENTS

| 3,578,405 | 5/1971 | Woodle ................... 23/253 R X |
| 3,811,842 | 5/1974 | Diebler et al. .......... 23/253 R X |

Primary Examiner—R.E. Serwin
Attorney, Agent, or Firm—Robert J. Steinmeyer; Robert R. Meads; John R. Shewmaker

[57] ABSTRACT

Apparatus for the analysis of samples such as blood or urine includes a reaction cell for reacting the sample with a chemical reagent at a predetermined temperature. A heat exchanger is provided on the reaction cell for establishing the temperature of the cell. Reagent is pumped into the cell through a conduit, and a portion of the conduit is wound around the reaction cell in contact with the heat exchanger to preheat reagent in the conduit before the reagent is pumped into the cell.

5 Claims, 2 Drawing Figures

TEMPERATURE CONTROL SYSTEM FOR CHEMICAL REACTION CELL

BACKGROUND OF THE INVENTION

1. Field of the Invention

The present invention relates generally to temperature control systems and, more particularly, to apparatus for controlling the temperature of a chemical reaction cell and of reaction components introduced into the cell. The apparatus of the invention is particularly useful in the analysis of biological samples, such as blood or urine, which are reacted with repeatable volumes of reagent at a predetermined temperature.

2. Description of the Prior Art

U.S. Pat. No. 3,857,771 (Sternberg), assigned to the assignee of the present invention, discloses chemical analysis apparatus for determining the glucose content of blood, urine, or other samples. In the apparatus, the sample is introduced into a reaction cell and reacted with a reagent such as glucose oxidase. A resulting rate of change of oxygen concentration is then measured to provide a measure of the glucose content in the sample.

U.S. Pat. No. 3,701,716 (Deuringer et al.), similarly assigned, discloses a semi-automated system for performing such analysis. In the Deuringer et al. system, a reproducible reagent volume is rapidly delivered from a reservoir to a reaction cell and a sample added to the reagent for reaction therewith. After analysis, the cell is completely drained in preparation for delivery of the next reagent volume thereto.

In practice, in the aforementioned systems a reagent volume on the order of 1 milliliter is first delivered to the reaction cell and a substantially smaller quantity of sample, on the order of ten microliters, is then injected into the cell by means of a pipette or other sampling device. Further, the analysis is carried out in a temperature controlled environment since the measurements are temperature sensitive. Typically, where body fluid samples are to be analyzed, the reaction is conducted near body temperature of 37° C. A temperature control system for such apparatus should preferably stabilize the temperature of the reaction cell and of the reagent therein prior to introduction of sample into the cell.

Several temperature control approaches have been employed with analysis apparatus of the foregoing type. In one approach the apparatus itself is enclosed within a temperature controlled housing so that the reaction chamber, the reagent reservoir, the delivery lines between the reservoir and the chamber, and other components are situated in an air bath. Thermal heaters and temperature sensors control the air bath temperature. This approach exhibits a number of disadvantages. First, a relatively large enclosure must be heated. As a result, the system exhibits a slow thermal response time and possible temperature variations at different locations within the enclosure. Moreover, the housing must be well insulated. In addition, opening the enclosure to gain access to the reaction chamber or other system components destroys the temperature equilibrium. Also, certain reagents rapidly deteriorate when maintained at elevated temperatures for prolonged periods, and such can occur when the reagent reservoir is situated within the enclosed air bath.

In a second approach, two separate heaters are employed, one to heat the reaction chamber to the proper temperature and the other to preheat the reagent in the delivery line at a location remote from the reaction chamber. While this approach can eliminate the need for an air bath housing, it requires two separate heaters each with an associated temperature sensor controlling operation thereof. As a result, relatively complex thermal control circuitry is required to control both heaters. Moreover, since the reagent preheater is remote from the reaction cell, the reagent temperature may drop in the time interval after the reagent is discharged from the preheater and before it is supplied to the reaction chamber. In such case, if proper reaction temperature is to be achieved, the reagent must be brought back up to the proper temperature after delivery to the reaction cell, thereby delaying the introduction of sample into the cell and reducing the sample throughput rate of the analyzer.

SUMMARY OF THE INVENTION

The present invention resides in new and improved temperature controller for a chemical reaction cell and a reaction component introduced into the cell which overcomes the disadvantages of the prior art. In its broader aspects the present invention contemplates a reaction cell having a chamber for receiving components of a chemical reaction, conduit means for supplying a reaction component from a reservoir to said chamber, and heat exchange means on at least a portion of the reaction cell and in contact with at least a portion of the conduit means for controlling both the temperature of the chamber and any contents thereof and the temperature of the portion of the conduit means and any reaction component therein. Means are provided for flowing the reaction component through the conduit means and the temperature controlled portion thereof to the reaction chamber. In this manner, a common heat exchanger may provide both preheating of the reaction component in the conduit means as well as temperature control of the reaction chamber.

DESCRIPTION OF THE PREFERRED EMBODIMENT

Figure 1:
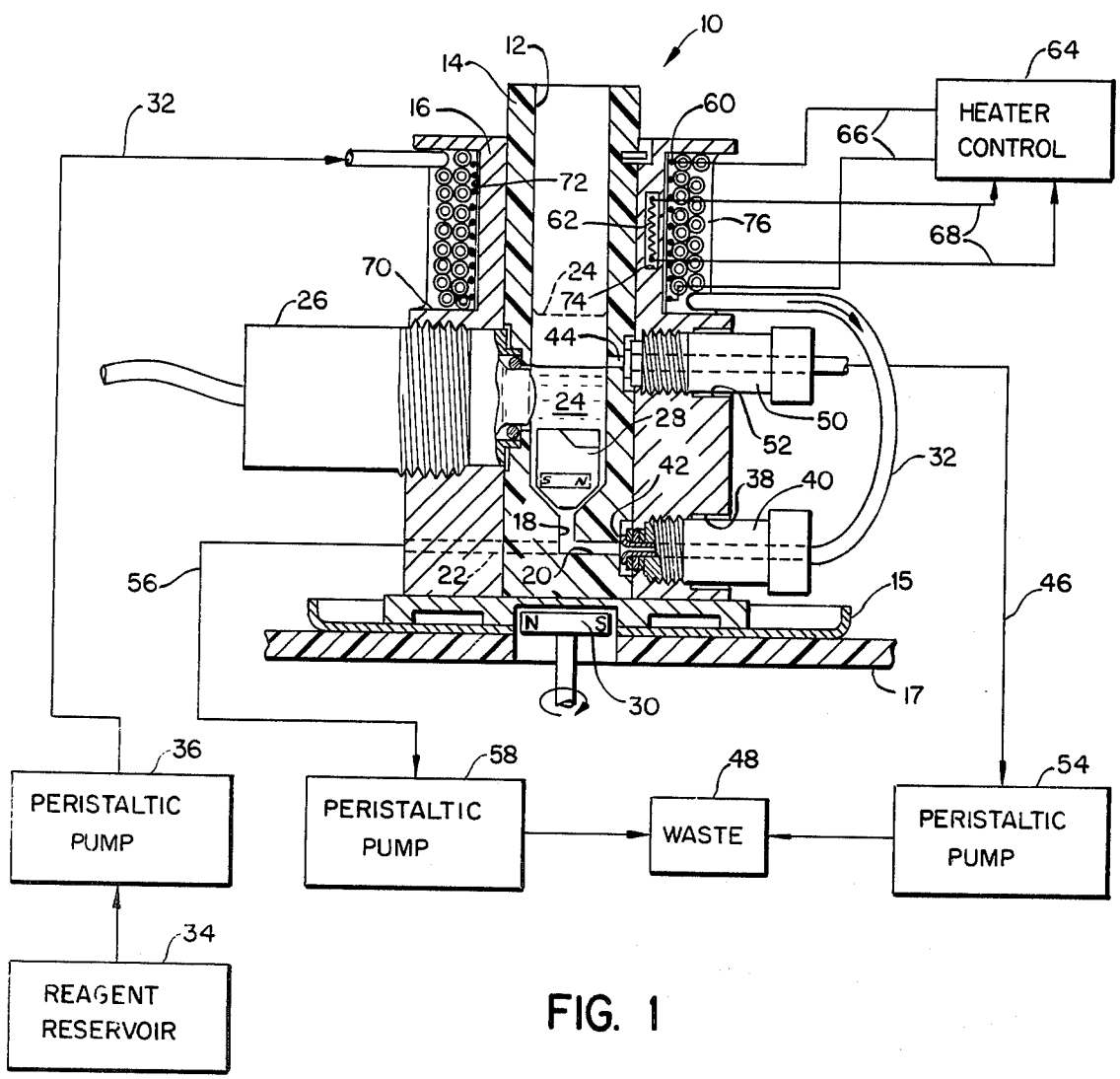
FIG. 1 is a combined block diagram and cross-sectional view, taken in a generally vertical plane, through a reaction cell incorporating the reagent delivery and the temperature control features of the present invention.

As illustrated in FIG. 1, the present invention is embodied in a reaction cell 10 illustrated as sitting within a spill tray 15 on a thermally insulating base or support 17. The body of the reaction cell includes an inner insulating cylinder 14 defining a cylindrical, vertically extending reaction chamber 12, and an outer jacket 16 surrounding and snugly engaging the wall of the inner cylinder. The reaction chamber 12 should be electrically nonconductive and inert with respect to chemicals introduced into the cell, and for this reason the inner cylinder 14 is preferably formed from a hydrophobic insulating material such as polytetrafluoroethylene, polychlorotrifluoroethylene, or polypropylene. The outer jacket 16 should be a good thermal conductor to establish, as nearly as possible, a constant thermal gradient along all portions of the reaction cell 12, and for this reason the jacket is preferably a metal such as aluminum. It should be understood, however, that, if desired, the entire reaction cell could be formed of metal and the walls of the reaction chamber 12 coated with one of the foregoing insulating materials, or the cell could be formed entirely from a thermally conductive electrically nonconductive material.

The reaction chamber 12 has an open top for receiving a pipette or other sample injection device in a fixed position for introducing quantities of sample material, such as blood or urine, into the chamber. The bottom of the reaction chamber has an inverted conical configuration and a vertically extending passage 18 communicates with the chamber at the apex of the chamber bottom. An inlet passage 20 and an outlet passage 22 lie in a generally horizontal plane and intersect passage 18. As will become apparent, a reaction component or reagent 24, such as glucose oxidase, is introduced into the reaction chamber 12 through passage 20 (and 18), and the contents of the reaction chamber are withdrawn from the chamber through passage 22 (and 18).

A liquid analysis sensor 26 extends through a bore in the wall of the reaction cell 10 with its sensing end in communication with the contents of the reaction chamber 12. For measuring the glucose concentration of a sample, the sensor 26 may be a polarographic oxygen sensor of conventional construction and as employed in the aforementioned U.S. Pat. Nos. 3,857,771 and 3,701,716. A magnetic stirring element 28 is positioned at the bottom of the reaction chamber for stirring the chamber contents and is rotated by a drive magnet 30 positioned beneath the reaction cell and rotated in a conventional manner. A preferred structure for magnetic stirring element is that disclosed in U.S. Pat. No. 3,591,309 (Ray et al.), assigned to the assignee of the present invention.

A conduit 32 connects inlet passage 20 in the bottom of the reaction cell 10 to a reservoir 34 containing the reagent 24 to be supplied to the reaction chamber 12. A pump 36, preferably of the peristaltic type, is provided for withdrawing reagent from the reservoir and for delivering the same through the conduit 32 into the reaction chamber 12 through passages 20 and 18. Conduit 32 is preferably formed from a length of flexible tubing of an inert material such as polytetrafluoroethylene. One end of conduit 32 is connected to peristaltic pump 36 while the opposite end of the conduit extends through a threaded horizontal bore 38 in the reaction cell wall and is supported therein by a threaded sleeve 40 in communication with inlet passage 20. For this purpose, the end of the conduit is outwardly flared to form an outwardly extending annular shoulder 42 which is compressed and sealed around the periphery of inlet passage 20 by the inward end of threaded sleeve 40 to provide a fluid tight seal therearound.

In order to establish a predetermined volume of reagent 24 in the reaction chamber 12, a horizontally extending sip port 44 is provided in the wall of the reaction cell and in communication with the reaction chamber. A conduit 46 connects port 44 to a waste reservoir 48. Conduit 46 may be a flexible tube like conduit 32. Conduit 46 is supported in communication with port 44 by a sleeve 50, identical to sleeve 40, threaded into a horizontally extending bore 52 in the reaction cell wall. A second peristaltic pump 54 is provided for withdrawing reagent 24 from the reaction cell through port 44 and conduit 46 to waste. If reagent 24 is initially supplied to chamber 12 above the level of port 44, as indicated by a dashed line in FIG. 1, actuation of pump 54 will withdraw reagent from the cell until the reagent level drops to the level of port 44 at which point only air can be withdrawn through the port and a predetermined volume of reagent remains in the chamber.

To drain the contents of the reaction chamber 12 after analysis, a conduit 56 is connected between discharge passage 22 and waste reservoir 48. Conduit 56 is supported by a threaded sleeve in a horizontally extending bore (neither shown) in communication with discharge passage 22 in a manner identical to conduits 32 and 46. A third peristaltic pump 58 connected to conduit 56 is provided to pump the contents of the chamber 12 to waste.

In accordance with the present invention, the reaction cell 10 includes heat exchange means on the reaction cell for controlling the temperature of the cell and of the reagent 24 delivered to the reaction chamber 12. The heat exchange means includes a heating element 60, a thermal sensor 62, and a heater control 64. The heater control is connected to the heating element by pair of conductors 66 and to the thermal sensor by a pair of conductors 68.

In order to accommodate the heat exchange means, the upper end of the reaction cell 10, and particularly outer jacket 16 thereof, includes an inwardly extending, annular recess 70 the inward surface 72 of which cylindrically surrounds the reaction chamber 12. With recess 70, the upper end of the reaction cell comprises a spool-shaped section. Heating element 60, such as nichrome heater wire, is wound a plurality of times around and on the cylindrical surface 72 within recess 70. Before winding the heating element, a strip of electrically insulating tape 73 (FIG. 2) may be wrapped around surface 72 to provide electrical insulation between the heating element and the body of aluminum jacket 16. The wall of jacket 16 includes a cut-out portion 74 between heating element 60 and reaction chamber 12 for receiving the thermal sensor 62. With this arrangement, heat generated by heating element 60 is conducted by jacket 16 throughout the length of reaction cell and the temperature at one point within the cell wall is monitored by sensor 62. Heater control 64 operates conventionally to energize heating element 60 in response to a feedback signal from thermal sensor 62 to maintain the cell temperature at a predetermined value.

Figure 2:
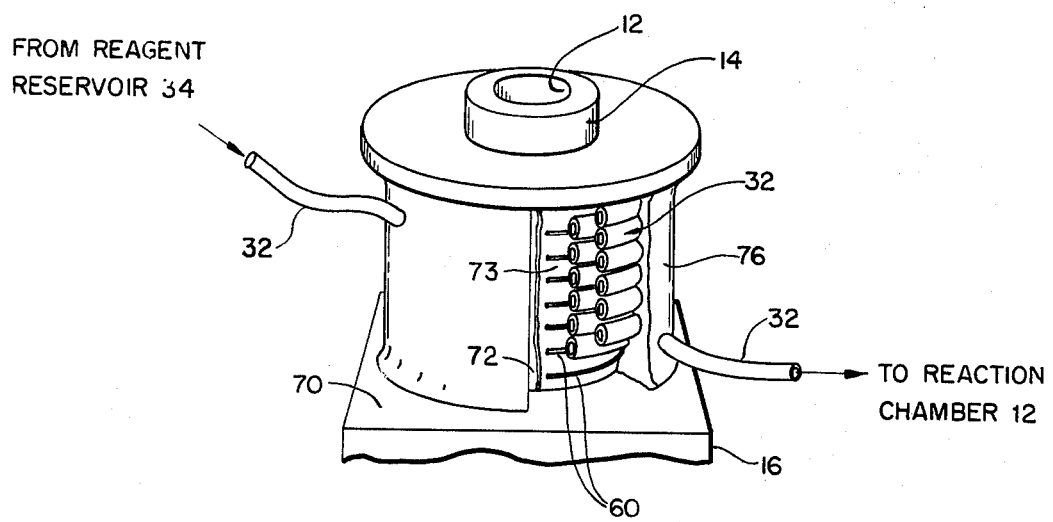
FIG. 2 is a fragmentary, perspective view of part of the reaction cell of FIG. 1, cut away in part to illustrate a heating element wound around the cell and a portion of a reagent delivery conduit wound around the cell and the heating element.

In accordance with an important aspect of the present invention, conduit 32, through which reagent 24 is supplied to the reaction chamber 12, is wound around the spool section of the reaction cell a plurality of times in contact with the heating element 60, as illustrated in the figures. Conduit 32 is potted in place around the heating element 60 by an epoxy 76 containing aluminum particles and filling the spaces between and around the conduit coils as illustrated in FIG. 2. In this manner, the heating element 60, in addition to heating the reaction cell wall, likewise heats this coiled portion of the reagent conduit 32 and any reagent contained in the conduit. As a result, the reagent 24 within the conduit is preheated and thus driven toward its desired predetermined temperature prior to being pumped into the reaction chamber.

In the preferred embodiment, where reagent volumes on the order of 1 milliliter are to be delivered to the reaction chamber 12, conduit 32 comprises tubing having inside and outside diameters of 0.040 in. and 0.075 in. respectively. Conduit 32 is wound around surface 72 within recess 70 a sufficient number of times so that the volume of reagent 24 within the wound conduit at least equals the predetermined reagent volume to be delivered to the reaction chamber.

In operation, and assuming that the reaction cell 12 is empty, peristaltic pump 36 is actuated to pump a predetermined quantity of reagent into the reaction chamber 12 to a level above sip port 44. The reagent thus delivered had been preheated prior to delivery in the coiled section of conduit 32 contacting the heating element 60. Thereafter, peristaltic pump 54 is actuated to withdraw reagent from the cell through sip port 44 until a predetermined reagent volume at the level of the sip port is established.

With the temperature of the reaction cell 10 and of the reagent 24 therein thus stabilized, an analysis operation proceeds by actuating the magnetic stirrer 28, injecting a predetermined volume of sample into the chamber 12 through the open top thereof for reaction with reagent 24, and monitoring the reaction by means of sensor 26 to provide a measure of the sample component of interest in a conventional manner. After completion of the analysis, peristaltic pump 58 is actuated to drain the contents of the cell. If desired, the cell may be then filled and drained one or more times with reagent 24 or a suitable rinse solution to completely rinse the chamber. Thereafter, the cycle is repeated and the chamber again filled with a predetermined reagent volume for a subsequent sample analysis. As before, the reagent thus introduced has been preheated in conduit 32 during the period when the prior sample analysis operation was being conducted. In practice and employing the preferred structure described hereinabove, a 1 milliliter volume of reagent is preheated from room temperature of about 22° C to a desired reaction temperature of about 37° C in about 30 seconds within the preheater configuration defined by the conduit 32.

From the foregoing it is evident that the present invention provides a temperature controller for a chemical reaction cell 10 and reaction component 24 to be reacted therein which employs a common heat exchanger for exchanging heat with both the cell and the reaction component. The arrangement eliminates the need for a controlled temperature air bath or for separate reaction cell and reaction component temperature control systems. Reagent reservoir 34 may even be refrigerated to prevent deterioration of the reagent before use. While the heat exchanger has employed a heating element 60 it will be understood that element 60 could alternately comprise a cooling element, such as a thermoelectric element, or comprise combinations of heating and cooling elements for applications requiring reduced temperatures.

In the specific embodiment of the invention, sensor 26 has been illustrated as a polarographic oxygen sensor as employed in the aforementioned patents. However, it should be understood that in addition to or instead of such an oxygen sensor, other sensing means such as electrochemical sensors or electrodes for electrolytic conductance measurement, could be mounted directly into the reaction chamber 12 in contact with the reagent therein. In addition, the reaction cell walls could be made optically transparent to permit optical sensing of light absorption, light scattering, fluorescence, or the like. The type of sensor will be determined by the type of analysis being performed and the nature of the chemical reaction being conducted. The advantages of the present invention in delivering predetermined volumes of reagent at controlled temperatures in a controlled temperature cell are present irrespective of the particular type of sensing means employed. Further, while a side port in the wall of the reaction chamber has been illustrated as defining the sip port 44, a vertical tube having its open lower end at the location of the side port could function as well and thus is intended to fall within the definition of a sip port as used herein.

Accordingly, while a preferred embodiment of the invention has been illustrated and described, it will be apparent that the foregoing as well as various other modifications may be made therein without departing from the spirit and scope of the invention as defined by the appended claims.

What is claimed is:

1. In combination:
   a reaction cell having a chamber for receiving components of a chemical reaction for reacting at a predetermined temperature;
   an inlet passage communicating with said chamber;
   a reaction component reservoir;
   conduit means connected between said reservoir and said inlet passage for supplying said reaction component to said chamber;
   heat exchange means including a heat exchange element on at least a portion of said reaction cell and in contact with at least a portion of said conduit means for exchanging heat with said chamber and any contents thereof and for exchanging heat with said portion of said conduit means and a quantity of reaction component therein, both said heat exchange element and said portion of said conduit means being disposed to surround said portion of said reaction cell; and
   means for flowing said reaction component through said conduit means toward said chamber and operative to maintain said quantity of reaction component in said portion of said conduit means for a period sufficient for said heat exchange means to drive the temperature of said reaction component toward said predetermined temperature prior to supplying said reaction component to said chamber.

2. The combination of claim 1 further including thermal sensing means proximate to said chamber, to said heat exchange element, and to said portion of said conduit means for controlling operation of said heat exchange means.

3. The combination of claim 1 wherein:
   said reaction cell includes a block having said reaction chamber extending generally vertically therein and an inwardly extending recess in said block surrounding said chamber and defining an outwardly facing cylindrical exterior surface of said block;
   said heat exchange element is wound around said cylindrical surface; and
   said portion of said conduit means comprises a tube wound around said cylindrical surface and said heat exchange element.

4. The combination of claim 1 wherein:
   said chamber extends generally vertically in said reaction cell; and
   said combination further includes
   a sip port communicating with said chamber at a vertical level intermediate the chamber top and bottom, and
   sip pump means connected to said sip port for pumping fluid out of said chamber through said sip port until the level of said fluid drops to the level of said sip port thereby establishing a repeatable, predetermined volume of reaction component in said chamber.

5. The combination of claim 1 wherein:
said reaction cell includes a block having said reaction chamber therein;
said heat exchange element is wound around said block surrounding said chamber; and
said portion of said conduit means comprises a tube wound around said block and said heat exchange element.

* * * * *